US00PP26675P3

(12) United States Plant Patent
Radler

(10) Patent No.: US PP26,675 P3
(45) Date of Patent: May 3, 2016

(54) SHRUB ROSE PLANT NAMED 'RADPASTEL'

(50) Latin Name: *Rosa hybrida*
Varietal Denomination: Radpastel

(71) Applicant: CP DELAWARE, INC., Wilmington, DE (US)

(72) Inventor: William J. Radler, Greenfield, WI (US)

(73) Assignee: CP DELAWARE, INC., Wilmington, DE (US)

( * ) Notice: Subject to any disclaimer, the term of this patent is extended or adjusted under 35 U.S.C. 154(b) by 141 days.

(21) Appl. No.: 14/121,069

(22) Filed: Jul. 28, 2014

(65) Prior Publication Data

US 2016/0029523 P1 Jan. 28, 2016

(51) Int. Cl.
*A01H 5/02* (2006.01)

(52) U.S. Cl.
USPC ..... Plt./104

(58) Field of Classification Search
USPC ..... Plt./101, 102, 104
See application file for complete search history.

*Primary Examiner* — Susan McCormick Ewoldt
(74) *Attorney, Agent, or Firm* — Buchanan Ingersoll & Rooney PC

(57) ABSTRACT

A new and distinct shrub rose plant is provided that abundantly and substantially continuously forms attractive single yellow blossoms that with maturity fade to blush pink. The plant exhibits vigorous vegetation and a rounding and bushy growth habit. The foliage is ornamental dark green with a semi-glossy finish on the upper surface. The light blossom coloration contrasts nicely with the dark green foliage. The disease resistance is excellent, particularly with respect to black spot, rust and mildews. The plant is well suited for providing attractive ornamentation in in the landscape.

1 Drawing Sheet

Botanical/commercial classification: *Rosa hybrida*/Shrub Rose Plant.

Varietal denomination: cv. Radpastel.

SUMMARY OF THE INVENTION

The new variety of *Rosa hybrida* landscape shrub rose plant of the present invention was created at Greenfield, Wis., U.S.A., by artificial pollination wherein two parents were crossed which previously had been studied in the hope that they would contribute the desired characteristics. The female parent (i.e., seed parent) was the 'Radquid' variety (non-patented in the United States), and the male parent (i.e., pollen parent) was the 'Radcor' variety (U.S. Plant Pat. No. 17,346). The parentage can be summarized as follows:

'Radquid'×'Radcor'.

The seeds resulting from the above pollination were sown and small plants were obtained which were physically and biologically different from each other. Selective study resulted in the identification of a single plant of the new variety.

It was found that the new Landscape Shrub rose plant of the present invention possesses the following combination of characteristics:

(a) abundantly and substantially continuously forms attractive single yellow blossoms that with maturity fade to blush pink,
(b) exhibits a rounding and bushy growth habit,
(c) forms vigorous vegetation,
(d) forms attractive ornamental dark green foliage with a semi-glossy finish on the upper surface that contrasts well with the blossom coloration,
(e) exhibits excellent disease resistance particularly with respect to black spot, rust and mildews, and (f) is well suited for growing as attractive ornamentation in the landscape.

A new rose variety is provided having attractive single yellow blossoms that assume a blush pink coloration with maturity, a rounded growth habit, and excellent disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors upon an inspection of the blossoms. More specifically, the 'Radquid' variety forms dissimilar yellow blossoms combined with a very short growth habit, and the 'Radcor' variety forms dissimilar coral pink blossoms having a yellow eye.

The new variety of the present invention also can be readily distinguished from other shrub rose plants including the 'Radsunny' variety (U.S. Plant Pat. No. 18,562) through an inspection of the blossoms. For instance, the yellow blossoms of the 'Radsunny' variety fade to dissimilar near white in the absence a blush pink coloration.

The characteristics of the new variety have been found at Wasco, Calif., U.S.A., to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radpastel'.

BRIEF DESCRIPTION OF THE PHOTOGRAPH

The accompanying photograph shows, as nearly true as it is reasonably possible to make the same in a color illustration of this character, a typical flowering specimen of the new variety. The illustrated rose plant of the new variety were approximately two years of age and were observed during May while growing outdoors on its own roots at West Grove, Pa., U.S.A. Buds and blossoms in various stages of maturity are illustrated together with the dark green semi-glossy foliage.

DETAILED BOTANICAL DESCRIPTION

The chart used in the identification of colors is that of The Royal Horticultural Society (R.H.S. Colour Chart—1995 Edition or equivalent), London, England. The description is based on the observation of two-year-old specimens of the new variety during October while growing outdoors on their own roots at West Grove, Pa., U.S.A.

Class: Landscape Shrub Rose. Cultivar 'Radpastel'.

Plant:

*Height.*—Commonly approach approximately 1 m on average at maturity.

*Width.*—Commonly approach approximately 1 m on average at maturity.

*Habit.*—Rounded and bushy.

Branches:

*Color.*—Near Green Group 138A on young stems, and commonly near Yellow-Green Group 146A on old wood.

*Thorns.*—Size: commonly approximately 4 mm in length on average when young, and approximately 6 mm in length on average when mature. Color: commonly near Yellow-Green Group 144C on young stems, and near Grey-Brown Group 199B when mature.

Leaves:

*Size.*—Commonly approximately 7.7 cm in length on average, and approximately 5.8 cm in width on average for a five-leaflet leaf.

*Leaflets.*—Number: 3, 5, and 7. Length: approximately 3.4 cm on average for a terminal leaflet, and approximately 2.3 cm on average for a lower leaflet. Width: approximately 2.2 cm on average for a terminal leaflet, and approximately 1.6 cm on average for a lower leaflet. Shape: ovate. Margins: serrate. Texture: generally smooth on the upper and under surfaces. Overall appearance: attractive dark green leaves with a semi-glossy upper surface. Color: (when young): Upper surface: near Green Group 137A. Under surface: near Green Group 137C. Color (when fully mature): Upper surface: near Green Group 139A. Under surface: near Green Group 139B.

Inflorescence:

*Number of flowers.*—Commonly in a cluster of approximately 3 to 5 blossoms per stem.

*Peduncle.*—Near Yellow-Green Group 144B in coloration, commonly approximately 2.8 cm in length on average, approximately 2 mm in diameter on average, and commonly covered with small flexible thorns less than 1 mm in length.

*Sepals.*—Upper surface: covered with short pubescence, and commonly near Green Group 143C in coloration. Under surface: commonly smooth, and commonly near Green Group 143A in coloration. Size: commonly approximately 2.9 cm in length on average, and approximately 6 mm in width at the base. Number: five.

*Buds.*—Shape: generally ovoid. Length: approximately 2 cm on average as the calyx breaks. Diameter: approximately 1.1 cm on average as the calyx breaks. Color: near Yellow Group 13C at the point of attachment, and near Red Group 39A at the apex.

*Flower.*—Form: single, cuplike. Diameter: commonly approximately 7 cm on average when fully open. Color (when opening begins): Upper surface: near Yellow Group 5A at the point of attachment, transitioning to near Yellow Group 8B at the apex. Under surface: near Yellow Group 10B at the point of attachment blending to Yellow Group 12C at the apex. Color (at end of blooming): Upper surface: near Yellow Group 11A at the point of attachment, transitioning to Yellow Group 11D, and finally to near Red Group 51D at the apex. Under surface: near Yellow Group 10B at the point of attachment blending to near Yellow Group 11D at the apex. Fragrance: none noticeable. Petal number: commonly approximately 10 on average under normal growing conditions. Petal length: commonly approximately 3.3 cm on average. Petal width: commonly approximately 3 cm on average. Petal shape: broadly obovate. Petal margin: entire. Petal apex: slightly cuspidate. Petal base: broadly cuneate. Petal drop: good, the petals commonly detach cleanly and freely drop upon full maturity. Stamen number: approximately 66 on average. Anthers: commonly near Yellow Group 13A in coloration. Filaments: approximately 6 mm in length, and the coloration is near Yellow Group 13C. Pollen: commonly present in a moderate quantity, and near Yellow Group 13A in coloration. Pistils: separate and free, and commonly number approximately 17 on average. Styles: commonly approximately 4 mm in size, and near Yellow Group 4D in coloration. Stigma: commonly less than 1 mm in size, and near Yellow Group 3B in coloration. Receptacle: commonly narrowly ovoid in shape, approximately 5 mm in diameter, smooth in texture, near Yellow-Green Group 144A in coloration, and with achenes commonly being present on the bottom and wall. Hips: substantially round in configuration, approximately 1.3 cm in diameter on average, and commonly near Orange Group 25A in coloration. Seeds: approximately 6 mm in length on average, approximately 4 mm in diameter on average, and near Greyed-Yellow Group 161A in coloration.

Development:

*Vegetation.*—Vigorous.

*Blossoming.*—Abundant and substantially, commonly with reflushing into late summer.

*Resistance to diseases.*—Excellent, particularly with respect to black spot, rust, and mildews.

Plants of the 'Radpastel' variety have not been observed under all possible environmental conditions to date. Accordingly, it is possible that the phenotypic expression may vary somewhat with changes in light intensity and duration, cultural practices, and other environmental conditions.

I claim:

1. A new and distinct Landscape Shrub rose plant characterized by the following combination of characteristics:

(a) abundantly and substantially continuously forms attractive single yellow blossoms that with maturity fade to blush pink, (b) exhibits a rounding and bushy growth habit, (c) forms vigorous vegetation, (d) forms attractive ornamental dark green foliage with a semi-glossy finish on the upper surface that contrasts well with the blossom coloration, (e) exhibits excellent disease resistance particularly with respect to black spot, rust and mildews, and (f) is well suited for growing as attractive ornamentation in the landscape;

substantially as herein shown and described.

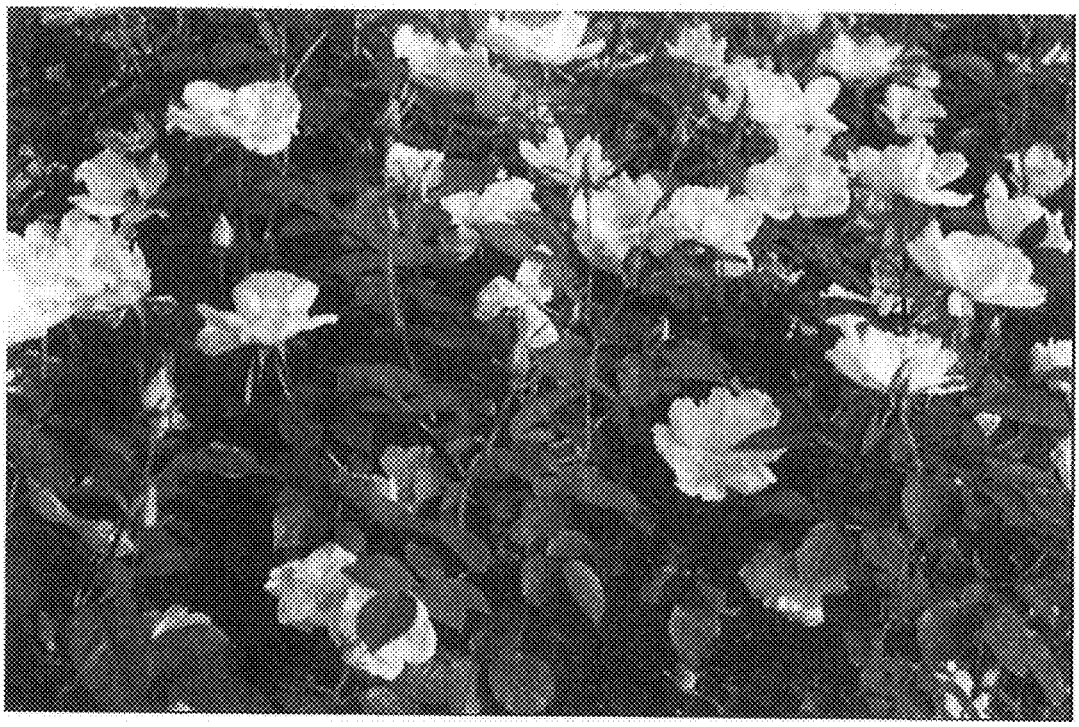

* * * * *